United States Patent
Bertsche et al.

(10) Patent No.: US 10,636,609 B1
(45) Date of Patent: Apr. 28, 2020

(54) BREMSSTRAHLUNG TARGET FOR RADIATION THERAPY SYSTEM

(71) Applicant: ACCURAY INCORPORATED, Sunnyvale, CA (US)

(72) Inventors: Kirk Joseph Bertsche, San Jose, CA (US); Giorgio Asmerom, San Jose, CA (US); Miguel Gutierrez, Milpitas, CA (US)

(73) Assignee: ACCURAY INCORPORATED, Sunnyvale, CA (US)

( * ) Notice: Subject to any disclaimer, the term of this patent is extended or adjusted under 35 U.S.C. 154(b) by 102 days.

(21) Appl. No.: 15/288,867

(22) Filed: Oct. 7, 2016

Related U.S. Application Data

(60) Provisional application No. 62/239,608, filed on Oct. 9, 2015.

(51) Int. Cl.
| | |
|---|---|
| *G01N 23/06* | (2018.01) |
| *H01J 35/08* | (2006.01) |
| *A61N 5/10* | (2006.01) |
| *A61B 6/00* | (2006.01) |

(52) U.S. Cl.
CPC .......... *H01J 35/08* (2013.01); *A61B 6/4435* (2013.01); *A61B 6/4458* (2013.01); *A61N 5/1081* (2013.01); *A61N 5/1083* (2013.01); *A61N 2005/1089* (2013.01); *H01J 35/116* (2019.05); *H01J 2235/081* (2013.01)

(58) Field of Classification Search
None
See application file for complete search history.

(56) References Cited

U.S. PATENT DOCUMENTS

| | | | |
|---|---|---|---|
| 3,999,096 A | 12/1976 | Funk et al. | |
| 5,420,905 A * | 5/1995 | Bertozzi | G01N 23/20091 378/86 |
| 6,463,123 B1 | 10/2002 | Korenev | |
| 2010/0195791 A1* | 8/2010 | Ishkhanov | H05H 7/12 378/57 |
| 2015/0243397 A1* | 8/2015 | Yun | G01N 23/20075 378/36 |

OTHER PUBLICATIONS

Zhang, R. et al. (Oct. 2013) "Superficial Dosimetry Imaging Based on Cerenkov Emission for External Beam Radiotherapy with Megavoltage X-ray Beam" Med. Phys. 40(10):101914-1-101914-12, 12 pages.
Gao, Q. et al. (2013) "Design and Optimization of the Target in Electron Linear Accelerator" Proceedings of IPAC2013, Shanghai, China THPWA016. 3 pages.
Odian, A. (Jul. 1966). "Point Target for Bremsstrahlung" TN-66-33, 5 pages.
Chao, A.W. (Mar. 26, 1999). "Electromagnetic and Nuclear Interactions". Handbook of Accelerator Physics and Engineering, Sec. 3.3: Particle-Matter Interaction, pp. 212-215.

(Continued)

*Primary Examiner* — Hoon K Song
(74) *Attorney, Agent, or Firm* — Womble Bond Dickinson (US) LLP; Daniel E. Ovanezian

(57) ABSTRACT

Described herein is a medical accelerator target including a target constructed of a material having an atomic number that is greater than or equal to 40 or having a thickness of less than 0.2 radiation lengths.

4 Claims, 5 Drawing Sheets

(56) References Cited

OTHER PUBLICATIONS

Chao, A.W. (Mar. 26, 1999). "Electromagnetic and Nuclear Interactions". Handbook of Accelerator Physics and Engineering, Sec. 3.3: Particle-Matter Interaction, pp. 598-601.
Olive, K.A. et al. (Aug. 21, 2014). "32. Passage of Particles through Matter" Chin. Phys. C38, 090001, 39 pages.
Definition of "Radiation length" from Wikipedia, the free encyclopedia, located at https://en.wikipedia.org/wiki/Radiation_length, downloaded on Nov. 1, 2018, 2 pages.
"Atomic and nuclear properties of tungsten (W)" located at http://pdg.lbl.gov/2017/AtomicNuclearProperties/HTML/tungsten_W.html, downloaded on Nov. 1, 2018, 1 page.

* cited by examiner

BREMSSTRAHLUNG TARGET FOR RADIATION THERAPY SYSTEM

RELATED APPLICATIONS

This application claims the benefit of U.S. Provisional Application No. 62/239,608, filed Oct. 9, 2015, the entire content of which is incorporated herein by reference.

TECHNICAL FIELD

Embodiments of the invention relate to a Bremsstrahlung target for radiation therapy.

BACKGROUND

Accelerator-based radiation therapy typically generates a high energy X-ray beam via bremsstrahlung ("braking radiation"). A relativistic electron beam is incident on a target material of high atomic number ("high Z"). The electrons are deflected (accelerated) by electromagnetic interactions with the target nuclei, causing emission of high energy photons. Some of these photons have enough energy to create electron-positron pairs, which then interact with target nuclei to emit more photons. The result is an "electromagnetic shower" or "electromagnetic cascade" of electrons, positrons, and photons. Any electrons which escape the target are typically eliminated from the therapy beam by an electron absorber made of low Z material (e.g. aluminum, carbon).

BRIEF DESCRIPTION OF THE DRAWINGS

Embodiments of the present invention are illustrated by way of example, and not by way of limitation, in the figures of the accompanying drawings.

DETAILED DESCRIPTION

Figure 1:
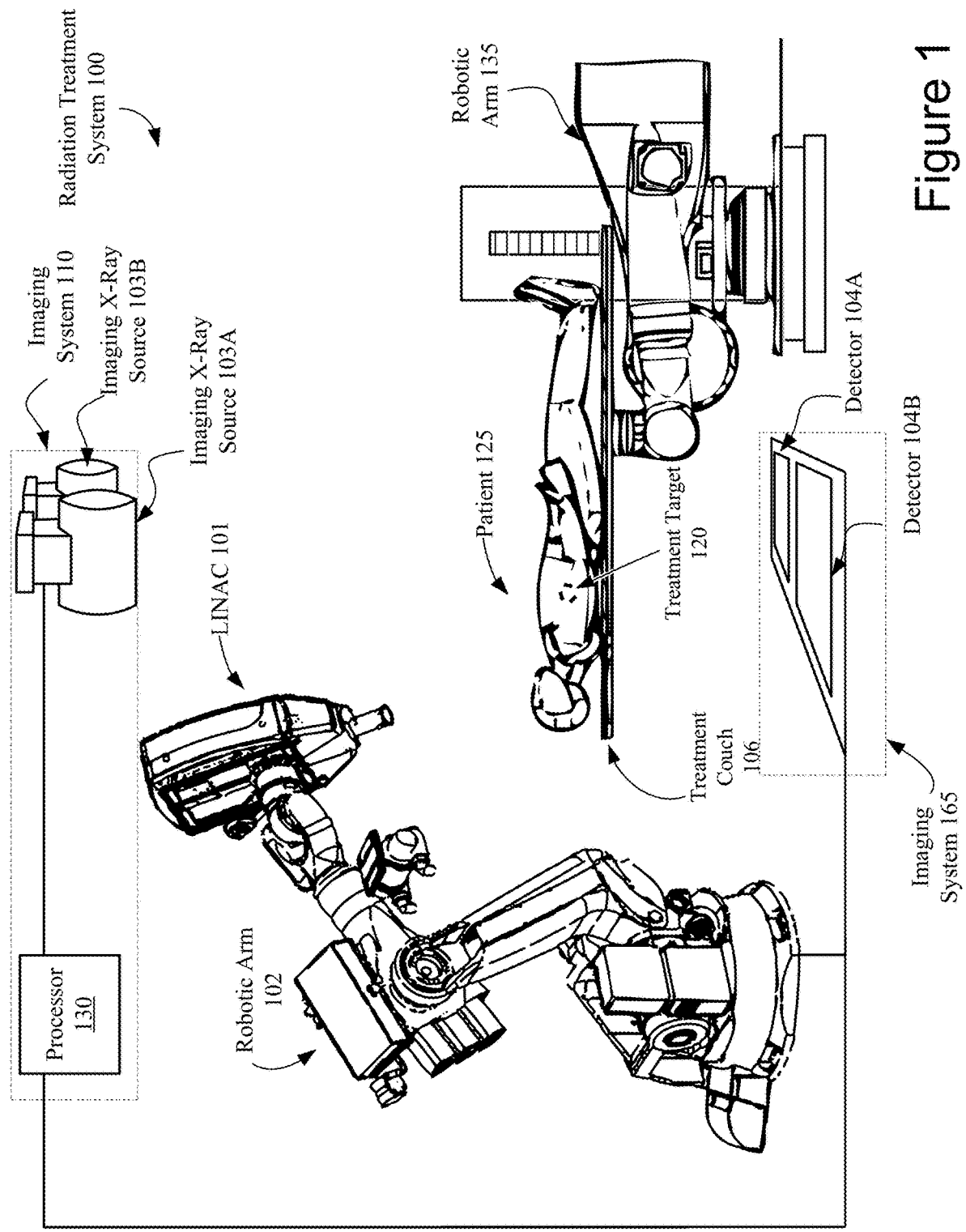
FIG. 1 illustrates an image-guided radiation treatment system, in accordance with embodiments of the present invention.

Embodiments of the present invention relate to a Bremsstrahlung target in a medical linear accelerator (LINAC) for radiation therapy. In an exemplary LINAC, electrons injected into an accelerator structure of the LINAC by an electron gun are accelerated and directed along the accelerator structure using the electric and magnetic field components of an electromagnetic wave that is coupled into the accelerator structure. The electromagnetic wave may be coupled into the accelerator structure from an amplifier, such as a klystron, or an oscillator, such as a magnetron. As the electrons traverse the accelerator structure, they are directed and accelerated by forces exerted on the electrons by the electric and magnetic field components of the electromagnetic wave to produce a high-energy electron beam. In some embodiments, the directing of the electrons may be assisted by static magnetic fields from solenoids, dipoles, quadrupoles or combined-function magnets. In other embodiments, the directing of the elections may not be assisted by static magnetic fields. The electron beam from the accelerator structure may be directed at an x-ray emitting target (referred to as a Bremsstrahlung target) to generate x-rays. Although embodiments of the present invention may be described using a traveling wave LINAC, it should be noted that embodiments of the present invention may also be utilized in any electron accelerator capable of reaching mega-electronvolt (MeV) beam energies. Examples of electron accelerators capable of reaching MeV beam energies include, but are not limited to, standing wave radio frequency (RF) LINACs, betatrons, dynamitrons, rhodotrons, synchrotrons and the like.

The x-ray emitting target is comprised of a material of high atomic number ("high Z"). As the thickness of the high Z target material is increased, the amount of radiation produced is increased. However, the high Z target material also absorbs radiation. If the thickness of the target is too thick, the result will be a decrease in total radiation flux. Therefore, in accordance with embodiments of the present invention, the LINAC is designed with a particular thickness for the high Z target material that balances photon production and absorption to maximize the total photon flux from the target, as will be discussed in more detail in FIG. 3 below.

The optimal thickness for the LINAC target may be expressed in terms of radiation length of the incident electrons in the high Z material. The radiation length is the mean distance over which a high-energy electron loses all but 1/e of its energy by bremsstrahlung. In one embodiment, the thickness of the target is in a range of 0.25 to 2 radiation lengths for bremsstrahlung targets without much variation of photon yield over this range of thicknesses. For example, the radiation length for a high energy electron in solid tungsten is approximately 3.5 millimeters (mm). Therefore, tungsten targets optimized for producing X-rays from relativistic electrons may be 0.9 to 7 mm in thickness.

As the electrons lose energy in the LINAC target, the energy density of the target increases. In order to prevent failure of the target it must be properly cooled. One method of cooling a LINAC target is to transfer energy from the target to a heat sink material with high thermal conductivity (e.g. copper) which is actively cooled with water. However, as therapy dose rates increase and as electron spot sizes are reduced to diminish penumbra, the energy density in the high Z material continues to increase, making cooling the high Z material difficult even when using the two-layer structure described above. A result may be the overheating and failure of a target.

An embodiment of the present invention resolves the cooling issue described above by minimizing the thickness of the high Z target. By minimizing the thickness of the LINAC target, the two-layer cooling structure is able to sufficiently cool the target at the increased therapy dose rates and electron spot sizes. The result being a LINAC capable of administering higher dose rates without overheating and failure of the high Z target.

The x-ray emitting target may be comprised of a material having a thermal conductivity of about 50 watts per meter-Kelvin (W/m·K) or higher in some implementations. For example, the x-ray emitting target may be comprised of a high Z target material having a thermal conductivity of about 50-400 W/m·K. Cooling of the x-ray emitting target may be facilitated by using a target material that has an increased thermal conductivity (e.g., a thermal conductivity of about 50 W/m·K or above). In other implementations, the x-ray emitting target may be comprised of a material having a thermal conductivity of about 8-400 W/m·K. Table 1 below lists some possible materials for the x-ray emitting target.

TABLE 1

Thermal Conductivities for Candidate Target Materials

| Material | Thermal Conductivity (W/m · K) |
| --- | --- |
| Aluminum | 204 |
| Copper | 386 |
| Tantalum | 54 |
| Tungsten | 165 |
| W25Re | 60 |
| Rhenium | 71 |
| Platinum | 73 |
| Gold | 315 |
| Mercury | 8 |
| Lead | 35 |
| Uranium | 24 |

Figure 5:
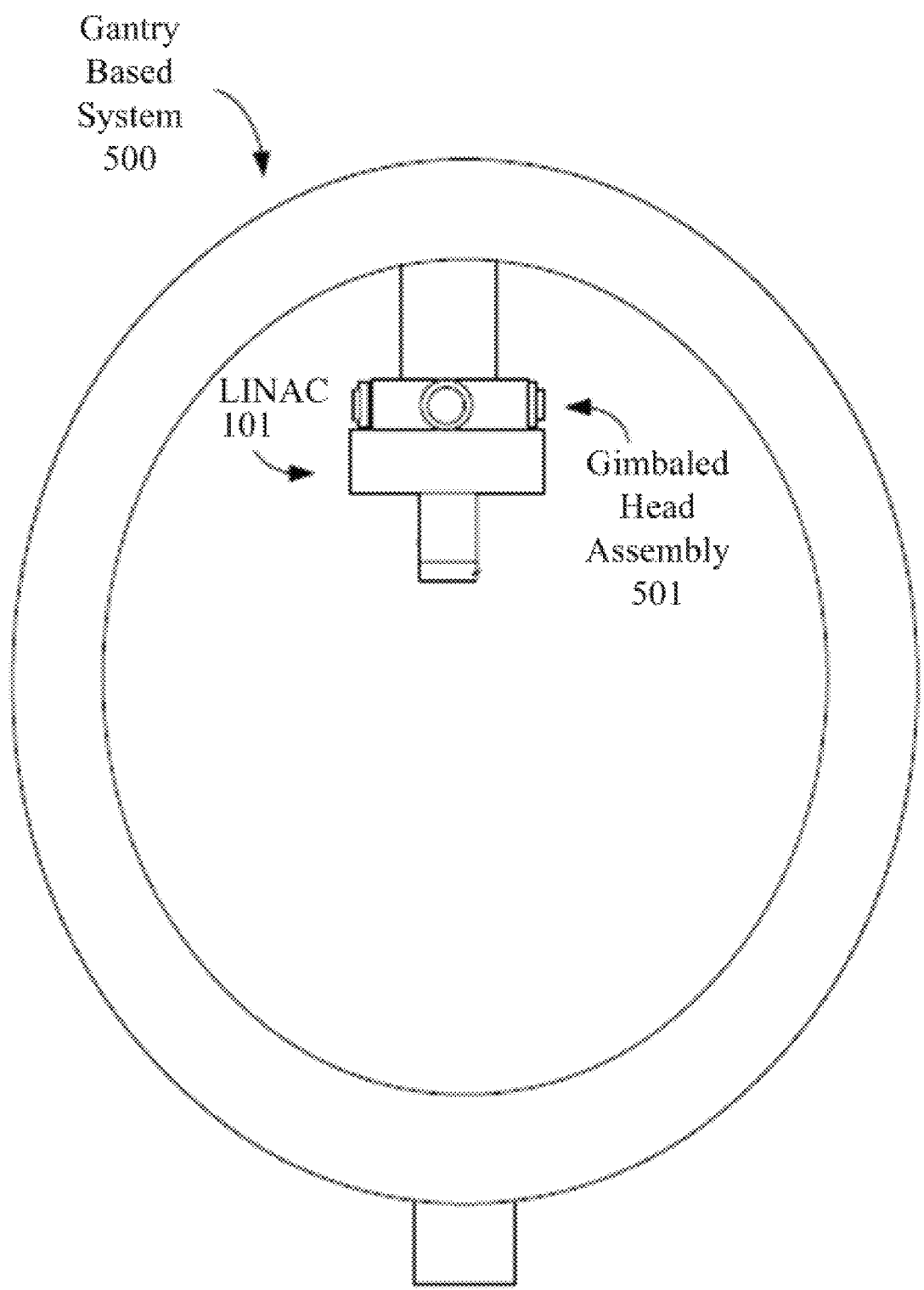
FIG. 5 illustrates a gantry based image-guided radiation treatment system, in accordance with embodiments of the present invention.

FIG. 1 illustrates an image-guided radiation treatment system, in accordance with embodiments of the present invention. In the illustrated embodiment, the radiation treatment system 100 includes a LINAC 101 that acts as a radiation treatment source. In one embodiment, the LINAC 101 may be a standing-wave LINAC. In an alternative embodiment, the LINAC 101 may be a traveling wave LINAC. In one embodiment, the LINAC 101 is mounted on the end of a robotic arm 102. In another embodiment, the LINAC 101 may be mounted on a gantry based system as illustrated in FIG. 5. LINAC 101 delivers one or more radiation treatment beams to a treatment target 120 within patient 125. In one embodiment the LINAC 101 may be an S-Band LINAC. In other embodiments the LINAC 101 may be a C-Band, X-Band or L-Band LINAC. FIG. 1 will be discussed in more detail below.

Figure 2:
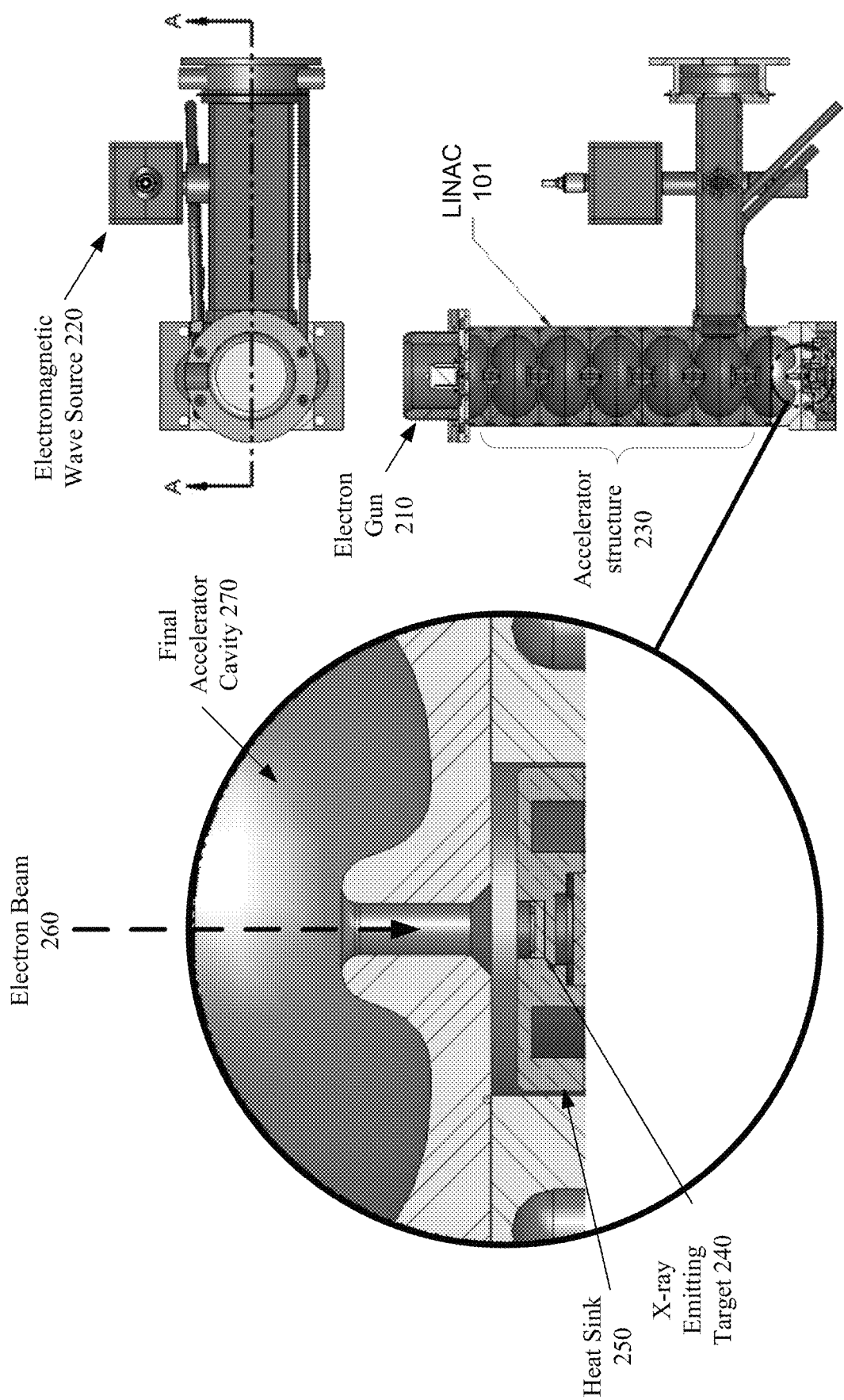
FIG. 2 illustrates a cross-section of a linear accelerator in accordance with one embodiment of the present invention.

FIG. 2 illustrates a cross-section of a LINAC in accordance with one embodiment of the present invention. In the illustrated embodiment, the LINAC 101 includes an electron gun 210. An example electron gun 210 includes an anode, a grid, a cathode and a filament. The filament is heated to cause the cathode to release electrons, which are accelerated away from the cathode and towards the anode at a high speed. The anode can focus the stream of emitted electrons into a beam of a controlled diameter. The grid can be positioned between the anode and the cathode.

The electromagnetic wave source 220 is a linear-beam vacuum tube that receives the electron beam from the electron gun 210 and generates high power electromagnetic waves (carrier waves). In one embodiment, the electromagnetic wave source 220 may be a magnetron. In another embodiment, the electromagnetic wave source 220 may be a klystron. The electromagnetic wave source 220 provides the driving force that powers the LINAC 101. The electron tube 220 coherently amplifies the input signal to output high power electromagnetic waves that have precisely controlled amplitude, frequency and input to output phase in the LINAC accelerator structure.

High power electromagnetic waves are injected into the accelerator structure 230 from the electron tube 220. The electrons enter the accelerator structure 230 and are typically bunched in the first few cells of the accelerator structure 230. The accelerator structure 230 is a vacuum tube that includes a sequence of tuned cavities separated by irises. The tuned cavities of the accelerator structure 230 are bounded by conducting materials such as copper to keep the energy of the high power electromagnetic waves from radiating away from the accelerator structure 230.

The tuned cavities are configured to manage the distribution of electromagnetic fields within the accelerator structure 230 and distribution of the electrons within the electron beam 260. The high power electromagnetic waves travel at approximately the same speed as the bunched electrons so that the electrons experience an accelerating electric field continuously. In the first portion of the LINAC 101, each successive cavity is longer than its predecessor to account for the increasing particle speed. The basic design criterion is that the phase velocity of the electromagnetic waves matches the particle velocity at the locations of the accelerator structure 230 where acceleration occurs.

Once the electron beam 260 has been accelerated by the accelerator structure 220 and passes through the final accelerator cavity 270, it can be directed at target 240 (e.g., constructed of a material such as a tungsten or copper) that is located at the end of accelerator structure 220. In one embodiment, the target 240 may be coupled to a heat sink 250 to aid in the cooling of the target 240. The target 240 and the heat sink 250 will be discussed in more detail in FIG. 4 below. The bombardment of the target 240 by the electron beam 260 generates a beam of x-rays (as discussed in FIG. 3 below). The electrons can be accelerated to different energies before striking the target 240. In one embodiment, the electron beam 260 may have a beam energy in the range of 4 to 25 MeV.

Figure 3:
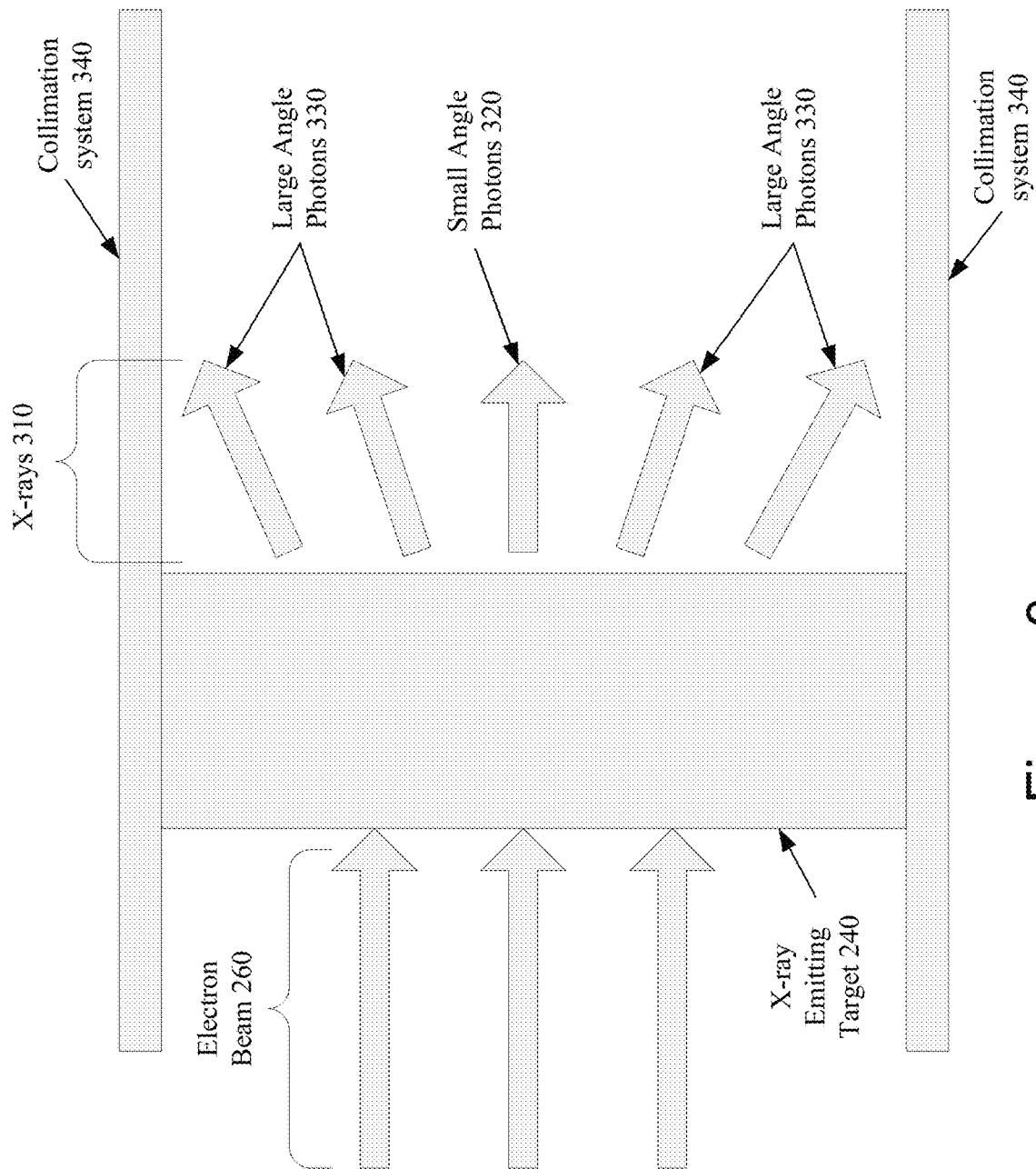
FIG. 3 illustrates an electron beam accelerated into a linear accelerator target to produce x-rays in accordance with an embodiment of the present invention.

FIG. 3 illustrates an electron beam 260 accelerated into a target 240 to produce x-rays. In the illustrated embodiment, an electron beam 260 is accelerated into a target 240, causing the emission of x-rays 310.

LINAC 101 only allows a small fraction of the total photons to pass through the system. Only those photons having small angles 320 with respect to the incident electron beam are kept, while photons having large angles 330 are absorbed by a collimation system 340. As the incident electrons interact with the target material, they scatter and fill an increasing solid angle. Most of the acceptable photons originate in the early interactions of an incident electron with the target 240. Following the early interactions, the incident electrons will typically have an angle that is too large to produce photons that will be accepted by the collimation system 340. For example, a 6 MeV electron beam will develop a route mean square (RMS) angular spread of approximately 15 degrees after passing through 0.01 radiation length of target material. After passing through 0.1 radiation length of target material, the RMS angular spread increases to approximately 45 degrees. While the electrons that are scattered throughout the large angles will continue to produce photons, very few of these photons will be accepted by the collimation system 340 and will contribute to therapy.

When the electrons have passed through a sufficient target thickness that the electron scattering angle exceeds the natural bremsstrahlung angle, the photon angular distribution will be dominated by the electron scattering angle. The electron scattering angle grows corresponding to the square root of the target thickness, resulting in the solid angle over which photons are emitted growing as the target thickness increases. The bremsstrahlung photon production also grows as the target thickness increases. Therefore, the photon density into a small collimated angle is roughly constant after the electron scattering angle exceeds the natural bremsstrahlung angle. In the previously described example, for a 6 MeV electron beam the electron scattering angle exceeds the natural bremsstrahlung angle at approximately 0.01 radiation length. As such, target 240 may be made thinner than conventional bremsstrahlung targets without loss of photon flux. Furthermore, there may be a resultant increase in photon flux due to lower photon absorption. Another advantage of the present embodiment is that a thinner target produces fewer total photons. Therefore, there will be less scattered radiation into electronics and other components, enabling radiation shielding thickness to be decreased.

Figures 4A, 4B:
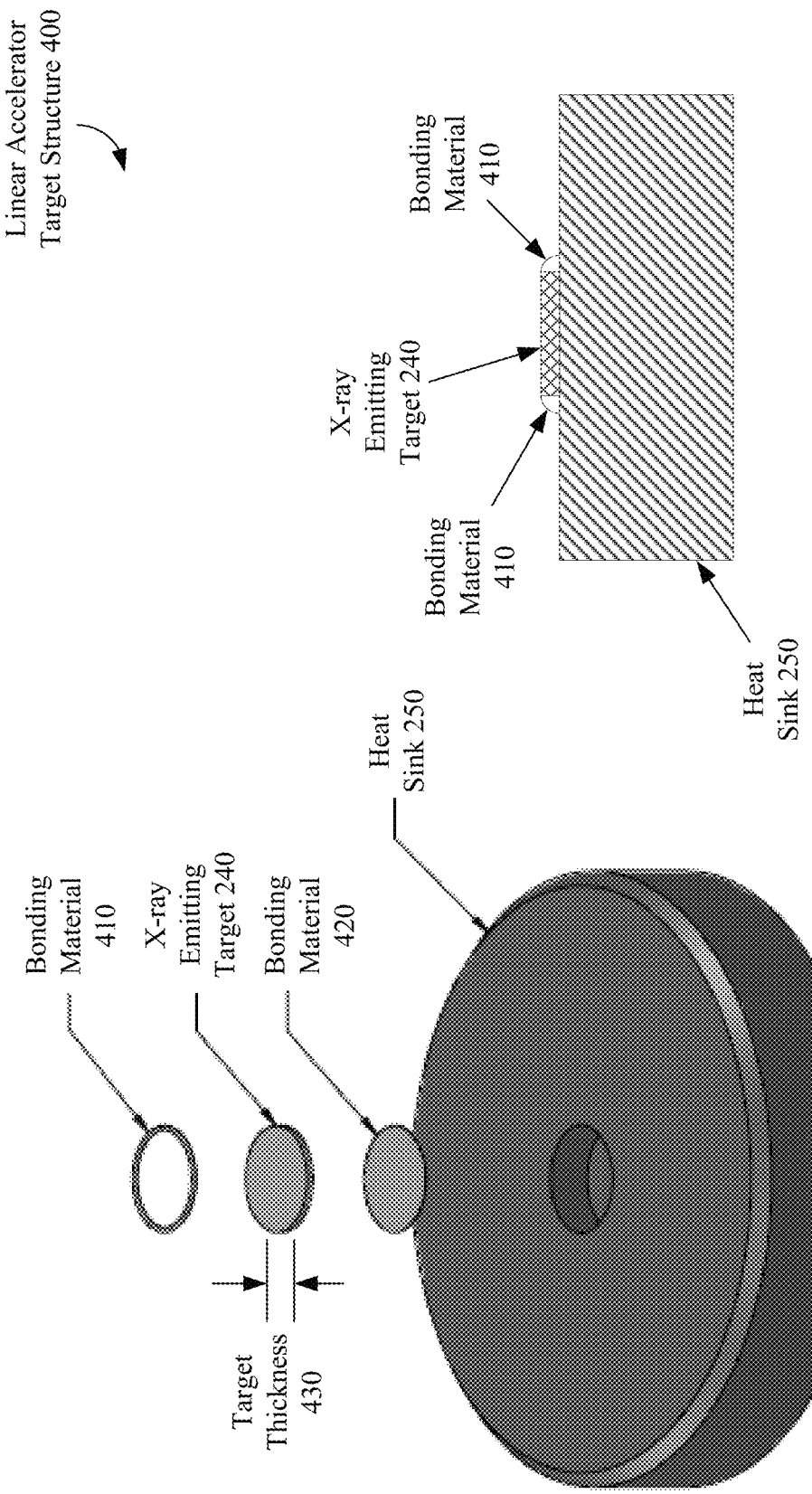
FIGS. 4A and 4B illustrate a linear accelerator target structure in accordance with embodiments of the present invention.

FIG. 4A illustrates one embodiment of a LINAC target structure. The illustrated embodiment of the LINAC target structure 400 includes bonding material 410, an x-ray emitting target 240 having a target thickness 430, bonding material 420 and a heat sink 250. In one embodiment, bonding materials 410 and 420 are brazing alloys used to braze the x-ray emitting target 240 to the heat sink 250. Examples of brazing alloys include, but are not limited to, aluminum, copper, brass, bronze, nickel, silver and the like. However, one skilled in the art would recognize the present invention may utilize other forms of bonding including, but not limited to, soldering, explosion bonding, diffusion bonding and the like. In an alternative embodiment, the LINAC target structure 400 does not include brazing material 410.

The x-ray emitting target 240 may be constructed from a metal material such as tungsten or a tungsten alloy. However, in alternative embodiments the LINAC target 240 may be comprised of any material having an atomic number greater than or equal to 40 (i.e. a high Z material). Examples of alternative materials for target 240 include, but are not limited to, tantalum, rhenium, platinum, gold, liquid mercury, liquid lead, uranium or any alloys or mixtures of high Z materials. In some embodiments the LINAC target 240 may be a circular disk. In other embodiments the LINAC target 240 may be a foil. The LINAC target 240 has a thickness 430 range of 0.01 to 0.2 radiation lengths. For example, in the present embodiment using a tungsten x-ray emitting target 240 having a radiation length of 3.5 mm, the target 240 would have an actual thickness 430 range of 0.035-0.7 mm. It should be noted that, while the thickness 430 range of 0.01 to 0.2 radiation lengths remains constant, the actual thickness 430 range of the target 240 will vary based on the target material used. In some embodiments the diameter of the target 240 may be the same diameter as the electron beam from the accelerator structure. In other embodiments the diameter of the target 240 may be larger than the electron beam diameter.

In the embodiment illustrated in FIG. 4A, the target 240 is located in a recessed portion of heat sink 250. FIG. 4B is a side profile view of an alternative embodiment where the heat sink 250 may not include a recessed portion, in which case the target 240 may be coupled to the surface of heat sink 250 by bonding material 410. In other embodiments, the LINAC target structure 400 may not include a heat sink 250 or brazing alloys 410 and 420 and be comprised solely of the target 240. The heat sink 250 is constructed from a material having a high thermal conductivity to aid in the cooling of the target 240. Examples of materials having a high thermal conductivity include, but are not limited to, copper, aluminum and brass.

Referring back to FIG. 1 illustrating configurations of image-guided radiation treatment system 100. In one embodiment, the LINAC 101 are mounted on the end of a robotic arm 102 having multiple (e.g., 5 or more) degrees of freedom in order to position the LINAC 101 to irradiate a pathological anatomy (e.g., treatment target 120 within patient 125) with beams delivered from many angles, in many planes, in an operating volume around a patient 125. Treatment may involve beam paths with a single isocenter, multiple isocenters, or with a non-isocentric approach. Alternatively, other types of image guided radiation treatment (IGRT) systems may be used. In one alternative embodiment, the LINAC 101 may be mounted on a gantry based system, for example, as illustrated in FIG. 5

The LINAC 101 may be positioned at multiple different nodes (predefined positions at which the LINAC 101 stops and radiation may be delivered) during treatment by moving the robotic arm 135. At the nodes, the LINAC 101 can deliver one or more radiation treatment beams to a treatment target 120. The nodes may be arranged in an approximately spherical distribution about a patient. The particular number of nodes and the number of treatment beams applied at each node may vary as a function of the location and type of pathological anatomy to be treated.

The radiation treatment system 100, in accordance with one embodiment of the present invention, includes an imaging system 165 having a processor 130 connected with x-ray sources 103A and 103B and fixed x-ray detectors 104A and 104B. Alternatively, the x-ray sources 103A, 103B and/or x-ray detectors 104A, 104B may be mobile, in which case they may be repositioned to maintain alignment with the treatment target 120 within patient 125, or alternatively to image the treatment target 120 from different orientations or to acquire many x-ray images and reconstruct a three-dimensional (3D) cone-beam CT. In one embodiment the x-ray sources are not point sources, but rather x-ray source arrays, as would be appreciated by the skilled artisan. In one embodiment, LINAC 101 serves as an imaging source (whether gantry or robot mounted), where the LINAC 101 power level is reduced to acceptable levels for imaging.

Imaging system 165 may perform computed tomography (CT) such as cone beam CT, and images generated by imaging system 165 may be two-dimensional (2D) or three-dimensional (3D). The two x-ray sources 103A and 103B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 106 during treatment) and to illuminate imaging planes of respective detectors 104A and 104B after passing through the patient 125. In one embodiment, imaging system 165 provides stereoscopic imaging of the treatment target 120 within patient 125 and the surrounding volume of interest (VOI). In other embodiments, imaging system 165 may include more or less than two x-ray sources and more or less than two detectors, and any of the detectors may be movable rather than fixed. In yet other embodiments, the positions of the x-ray sources and the detectors may be interchanged. Detectors 104A and 104B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

FIG. 5 illustrates one embodiment of a gantry based (isocentric) intensity modulated radiotherapy (IMRT) system 500. In a gantry based system 500, a radiation source (e.g., a LINAC 101) having a head assembly 501 are mounted on the gantry in such a way that they rotate in a plane corresponding to an axial slice of the patient. Radiation is then delivered from several positions on the circular plane of rotation. In IMRT, the shape of the radiation beam is defined by a multi-leaf collimator (MLC) that allows portions of the beam to be blocked, so that the remaining beam incident on the patient has a pre-defined shape. The resulting system generates arbitrarily shaped radiation beams that intersect each other at the isocenter to deliver a dose distribution to the treatment target 120. In one embodiment, the gantry based system 500 may be a C-arm based system.

Unless stated otherwise as apparent from the foregoing discussion, it will be appreciated that terms such as "processing," "computing," "generating," "comparing" "determining," "calculating," "performing," "identifying," or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A medical traveling wave linear accelerator comprising:
    a klystron to receive a beam current of electrons and to generate an electromagnetic wave;
    an accelerator structure to receive the electromagnetic wave and to generate an output therapy dose rate of electrons having a beam energy between 4-25 megaelectronvolts (MeV); and
    an accelerator target structure to receive the output dose of electrons comprised of:
        an x-ray emitting target to emit x-rays in response to receiving the output dose rate of electrons, wherein the x-ray emitting target is less than 0.2 radiation lengths; and
        a heat sink coupled to the x-ray emitting target.

2. The traveling wave linear accelerator of claim 1, wherein the thickness of the x-ray emitting target is between 0.01 and 0.2 radiation lengths.

3. The medical traveling wave linear accelerator of claim 1, wherein the accelerator is coupled to a robotic arm.

4. The medical traveling wave linear accelerator of claim 1, wherein the accelerator is coupled to a gantry.

* * * * *